US00PP33196P2

(12) United States Plant Patent
Smit

(10) Patent No.: US PP33,196 P2
(45) Date of Patent: Jun. 22, 2021

(54) ***ALOE* PLANT NAMED 'EC-ALAC-2001'**

(50) Latin Name: *Aloe aculeata*
Varietal Denomination: EC-ALAC-2001

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/036,647

(22) Filed: Sep. 29, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

(56) References Cited

PUBLICATIONS

UPOV hit on *Aloe* plant named, 'EC-ALAC-2001', QZ PBR 20200907, filed Mar. 31, 2020.*

* cited by examiner

*Primary Examiner* — Anne Marie Grunberg
(74) *Attorney, Agent, or Firm* — Cassandra Bright

(57) ABSTRACT

A new and distinct cultivar of *Aloe* plant named 'EC-ALAC-2001' is disclosed, characterized by leaves with distinctive raised oblong ridges colored Greyed-Green 193B with center near Orange-Red 35C and a serrate light red margin over a bright green background leaf color. Plants have a uniquely broad base, with foliage becoming upright, forming a distinctly tulip-shaped rosette. The new variety is an *Aloe*, typically produced as an indoor or outdoor ornamental plant.

3 Drawing Sheets

Latin name of the genus and species: *Aloe aculeata.*
Variety denomination: 'EC-ALAC-2001'.

BACKGROUND OF THE INVENTION

The new cultivar is a product of a planned breeding program. The seed parent an unpatented proprietary *Aloe aculeata* hybrid referred to as '12AL-34'. The pollen parent an unpatented proprietary *Aloe aculeata* hybrid referred to as '12AL-38'. The crossing was made during 2013 in Sappemeer, The Netherlands at a commercial greenhouse. 'EC-ALAC-2001' was discovered by the inventor in 2014.

Asexual reproduction of the new cultivar 'EC-ALAC-2001' was first performed in Sappemeer, The Netherlands, at a commercial laboratory by tissue culture in September of 2014. 'EC-ALAC-2001' has since produced several generations and has shown that the unique features of this cultivar are stable and reproduced true to type.

SUMMARY OF THE INVENTION

The cultivar 'EC-ALAC-2001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-ALAC-2001'. These characteristics in combination distinguish 'EC-ALAC-2001' as a new and distinct *Aloe* cultivar:

1. Distinctive raised oblong ridges colored Greyed-Green 193B with center near Orange-Red 35C on foliage.

2. Serrate light red margin and bright green background leaf color.
3. Broad plant base, with foliage becoming upright, forming a distinctly tulip-shaped rosette.

PARENTAL COMPARISON

Plants of the new cultivar 'EC-ALAC-2001' are similar to the seed parent in most horticultural characteristics. However, plants of the new variety differ from the seed parent in the following:

1. New cultivar has a light red serrate margin, the seed parent does not have a colored margin.
2. The new variety has distinctly raised stripes, the seed parent has stripes which are not raised.

Plants of the new cultivar 'EC-ALAC-2001' are similar to the pollen parent in most horticultural characteristics. However, plants of the new variety differ in the following:

1. New cultivar has a light red serrate margin; the pollen parent has a red margin.
2. New variety forms a broad base of the plant, then foliage becomes upright, the pollen parent plant shape is upright.
3. The new variety has distinctly raised stripes, the pollen parent has stripes which are not raised.

COMMERCIAL COMPARISON

'EC-ALAC-2001' can be compared to the unpatented commercial variety *Aloe* 'Spider'. The two *Aloe* varieties are similar in most horticultural characteristics; however, the new variety differs in the following:

1. New cultivar has wider foliage than this comparator.
2. Plants of the new variety have a rosette formation; plants of this comparator form multiple growth points.
3. The new variety has distinctly raised stripes, this comparator has stripes which are not raised.
4. This comparator does not have the serrate light red margin of the new variety.

'EC-ALAC-2001' can also be compared to the commercial variety *Aloe* 'EC-ALOE-1801', U.S. Plant Pat. No. 31,336. The two *Aloe* varieties are similar in most horticultural characteristics; however, the new variety differs in the following:

1. New cultivar has light red marginal serrations, this comparator has darker red and thicker marginal serration.
2. The new variety has dark green foliage with many light green stripes, foliage of this comparator is solid green.
3. Leaf tip aspect of the new variety bends slightly inward, leaf tip aspect of this comparator bds slightly downwards.

BRIEF DESCRIPTION OF THE PHOTOGRAPHS

The accompanying photograph in FIG. 1 illustrates in full color a typical plant of 'EC-ALAC-2001' grown in a greenhouse in Sappemeer, The Netherlands. This plant is approximately 11 months old, shown in a 10.5 cm container.

Figure 1:
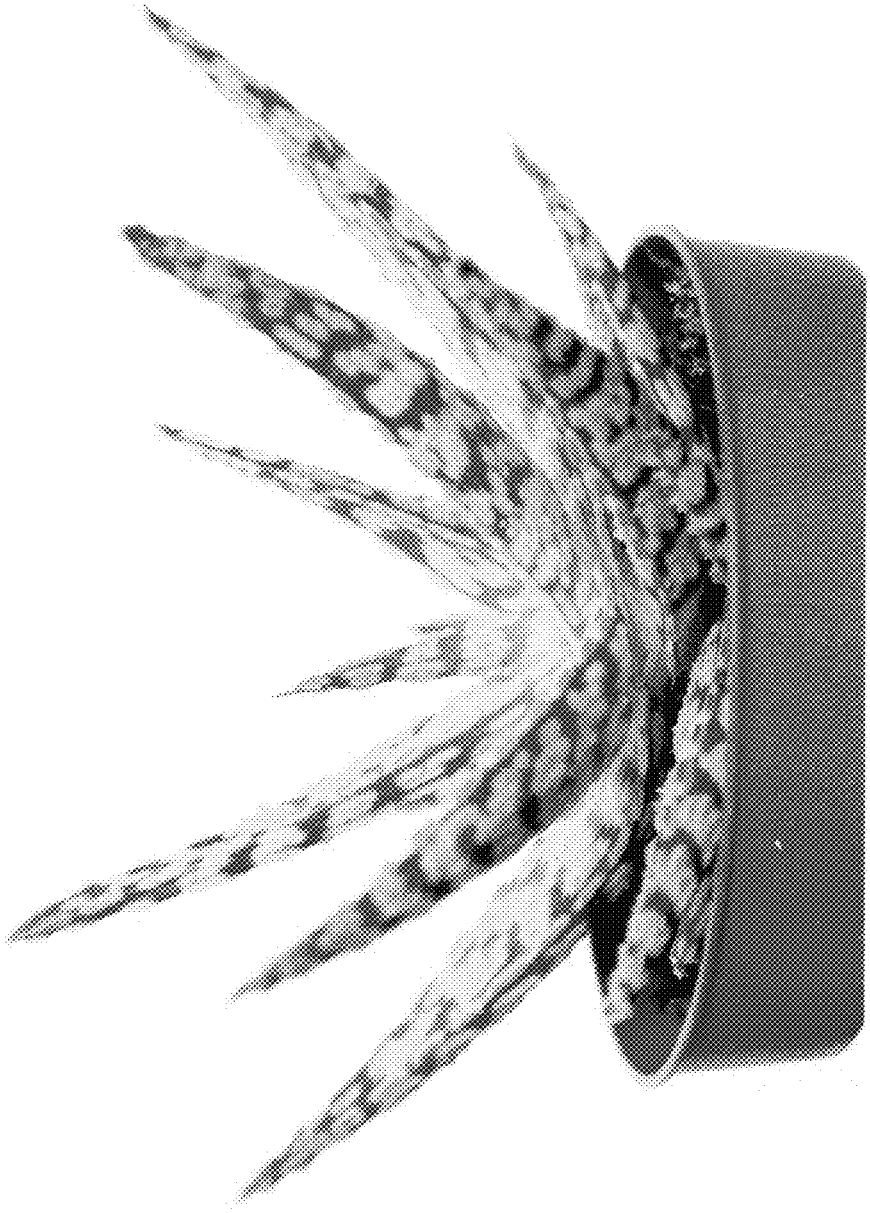
Figure 2:
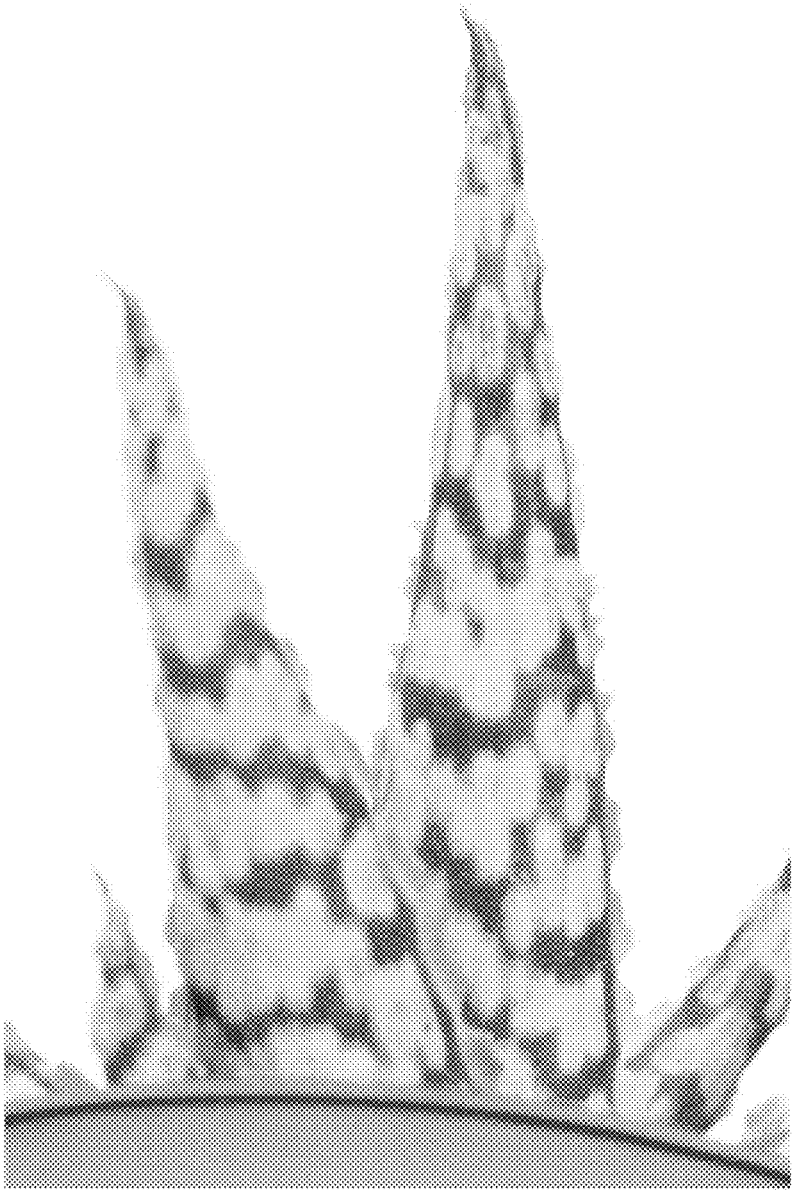
FIG. 2 illustrates a close up view of the underside of the foliage.
Figure 3:
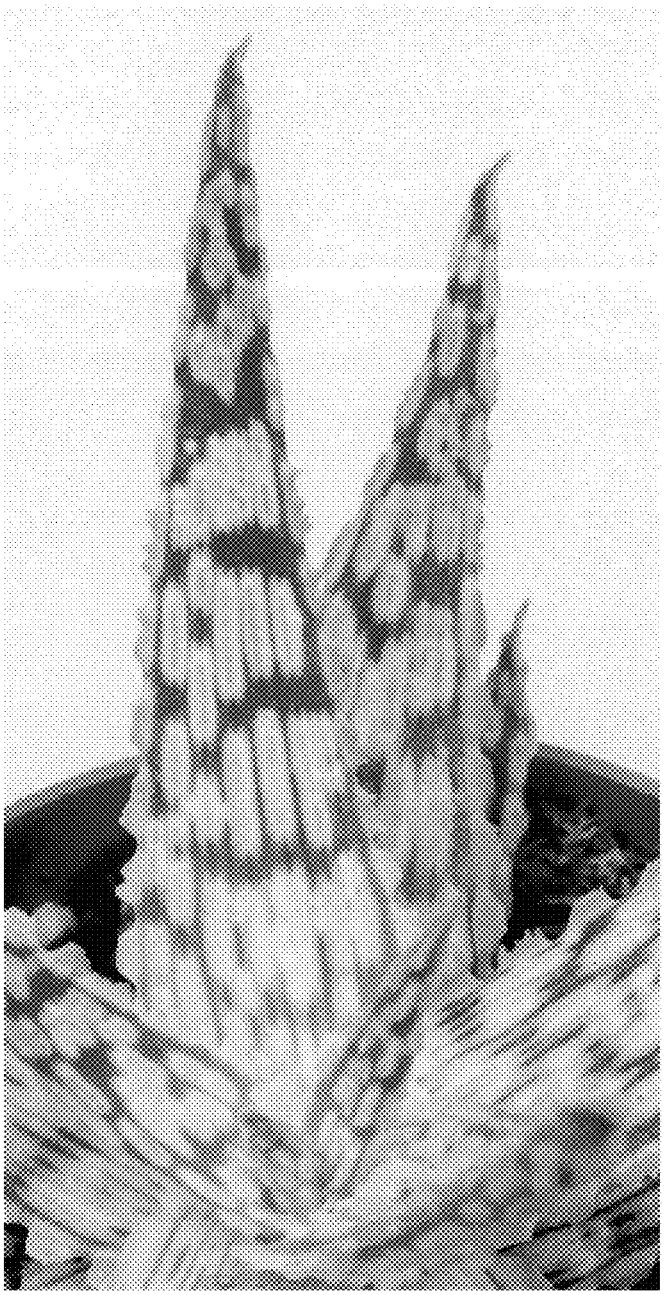
FIG. 3 illustrates a close up view of the upperside of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 edition, except where general terms of ordinary dictionary significance are used. The following observations and measurements describe 'EC-ALAC-2001' plants in a commercial greenhouse in Sappemeer, The Netherlands during April. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'EC-ALAC-2001'.

Age of the plant described: 11 months in a 10.5 cm pot.

PROPAGATION

Time to initiate roots: Approximately 7 to 10 days at 20° C.

Time to produce a rooted liner: About 28 to 35 days at 20° C.

Propagation method: Tissue culture.

PLANT

Growth habit: Basal rosette with a broad base, then foliage turning upright, forming tulip shape.

Container size: 10.5 cm.

Height: 9.6 cm to top of foliar plane.

Plant spread: Average 15.1 cm.

Growth rate: Low to moderate.

Branching characteristics: Single basal rosette. No branches.

Root description: Moderately dense, fibrous. White, around RHS 155A.

FOLIAGE

Leaf:

*Arrangement.*—Rosette.

*Quantity of leaves.*—Approximately 15 per rosette.

*Average length.*—9.1 cm.

*Average width.*—2.4 cm.

*Average thickness.*—0.55 cm.

*Shape of blade.*—Lanceolate, succulent.

*Apex.*—Long acuminate.

*Base.*—Broad cuneate.

*Margin.*—Coarsely dentate-serrate. Average length of teeth: 0.15 cm, average width of teeth: 0.3 cm, colored Red 37A.

*Aspect.*—Upright, slightly concave with a slight outward arch in apical section.

*Texture of upper surface.*—Pustulate, visible as narrow oblong ridges, colored orange-red in between 35C, ridges margined greyed-green; 193B, average length of ridges: 0.4 cm, average diameter of ridges: 0.15 cm, average height of ridges: 0.075 cm.

*Texture of under surface.*—Pustulate, visible as narrow oblong ridges, colored greyed-green; 193A, average length of ridges: 0.3 cm, average width of ridges: 0.15 cm, average height of ridges; less than 0.05 cm.

*Appearance upper surface.*—Moderately glossy.

*Appearance under surface.*—Moderately glossy.

*Color.*—Young foliage upper side: Green to yellow-green; in between 143A and 144A, fading lighter towards the base; 144B and 144C. Oblong ridges colored Greyed-Green 193B with center near Orange-Red 35C. Margin near Red 37A. Young foliage under side: Near RHS Green; N143A, fading lighter towards the base; Yellow-Green 144B. Oblong ridges colored Greyed-Green 193B with center near Orange-Red 35C. Margin near Red 37A. Mature foliage upper side: Near RHS Green; NN137B, fading lighter towards the base; near Green 137B. Oblong ridges colored Greyed-Green 193B with center near Orange-Red 35C. Margin near Red 37A. Mature foliage under side: Near RHS Green; NN137B, fading lighter towards Green 137B. Oblong ridges colored Greyed-Green 193B with center near Orange-Red 35C. Margin near Red 37A.

Venation: Parallel venation, coloration indistinguishable from leaf blade.

FLOWER

Flowering: Not observed.

OTHER CHARACTERISTICS

Seeds and fruits: None observed to date.

Temperature tolerance: Tolerates temperatures up to 40 degrees C.

Disease/pest resistance: Neither resistance nor susceptibility to normal diseases and pests known to *Aloe* observed to date.

What is claimed is:

1. A new and distinct cultivar of *Aloe* plant named 'EC-ALAC-2001' as herein illustrated and described.

* * * * *